US00PP26608P3

(12) United States Plant Patent
Knosher

(10) Patent No.: US PP26,608 P3
(45) Date of Patent: Apr. 12, 2016

(54) ***HELIOPSIS* PLANT NAMED 'DOUBLE SUNSTRUCK'**

(50) Latin Name: *Heliopsis helianthoides*
Varietal Denomination: Double Sunstruck

(71) Applicant: Ball Horticultural Company, West Chicago, IL (US)

(72) Inventor: Lynne Knosher, Campton Hills, IL (US)

(73) Assignee: Ball Horticultural Company, West Chicago, IL (US)

( * ) Notice: Subject to any disclaimer, the term of this patent is extended or adjusted under 35 U.S.C. 154(b) by 99 days.

(21) Appl. No.: 14/121,359

(22) Filed: Aug. 25, 2014

(65) Prior Publication Data

US 2016/0057917 P1 Feb. 25, 2016

(51) Int. Cl.
*A01H 5/02* (2006.01)

(52) U.S. Cl.
USPC ..... Plt./437

(58) Field of Classification Search
USPC ..... Plt./437
See application file for complete search history.

*Primary Examiner* — June Hwu
(74) *Attorney, Agent, or Firm* — Audrey Charles

(57) ABSTRACT

A new and distinct cultivar of *Heliopsis* plant named 'Double Sunstruck', characterized by its semi-double type, dark yellow-colored inflorescences, green and white variegated foliage, and moderately vigorous, compact-mounded growth habit, is disclosed.

1 Drawing Sheet

Latin name of genus and species of plant claimed: *Heliopsis helianthoides*.
Variety denomination: 'Double Sunstruck'.

BACKGROUND OF THE INVENTION

The present invention relates to a new and distinct cultivar of *Heliopsis* plant botanically known as *Heliopsis helianthoides* and hereinafter referred to by the cultivar name 'Double Sunstruck'.

The new cultivar originated in a controlled breeding program in Elburn, Ill. during March 2010. The objective of the breeding program was the development of *Heliopsis* cultivars having large flowers, novel foliage color, and compact habits.

The new *Heliopsis* cultivar is the result of cross-pollination. The female (seed) parent of the new cultivar is the proprietary *Heliopsis helianthoides* breeding selection coded 3652-C3, not patented, characterized by its single-type, dark yellow-colored inflorescences, green and white variegated foliage, and minimally vigorous, upright growth habit. The male (pollen) parent of the new cultivar is the proprietary *Heliopsis helianthoides* breeding selection coded 3645-A2, not patented, characterized by its double-type, dark yellow-colored inflorescences, medium green-colored foliage, and moderately vigorous, upright growth habit. The new cultivar was discovered and selected as a single flowering plant within the progeny of the above stated cross-pollination during August 2012 in a controlled environment in Elburn, Ill.

Asexual reproduction of the new cultivar by terminal stem cuttings since August 2012 in Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Double Sunstruck' as a new and distinct cultivar of *Heliopsis* plant:

1. Semi-double type, dark yellow-colored inflorescences;
2. Green and white variegated foliage; and
3. Moderately vigorous, compact-mounded growth habit.

Plants of the new cultivar differ from plants of the female parent primarily in flower form and growth vigor and from plants of the male parent primarily in foliage color and plant height. The new cultivar is shorter than the male parent.

Of the many commercially available *Heliopsis* cultivars, the most similar in comparison to the new cultivar is 'Sunstruck', U.S. patent application Ser. No. 13/987,854. However, in side by side comparisons, plants of the new cultivar differ from plants of 'Sunstruck' in at least the following characteristics:

1. Plants of the new cultivar have more ray florets than plants of 'Sunstruck'; and
2. Plants of the new cultivar have larger inflorescences than plants of 'Sunstruck'.

In addition the new cultivar can be compared to 'Loraine Sunshine', U.S. Plant Pat. No. 10,690. However, in comparison, plants of the new cultivar differ from plants of 'Loraine Sunshine' in at least the following characteristics:

1. Plants of the new cultivar are shorter than plants of 'Loraine Sunshine';
2. Plants of the new cultivar have more ray florets than plants of 'Loraine Sunshine'; and
3. Plants of the new cultivar have a ray floret color that is more orange-colored than plants of 'Loraine Sunshine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Double Sunstruck' The plants were grown in 1.5 gallon containers for approximately two months in a greenhouse and 11 weeks outdoors in West Chicago, Ill. Plants were given two pinches prior to transplant.

DETAILED BOTANICAL DESCRIPTION

Figure 1:
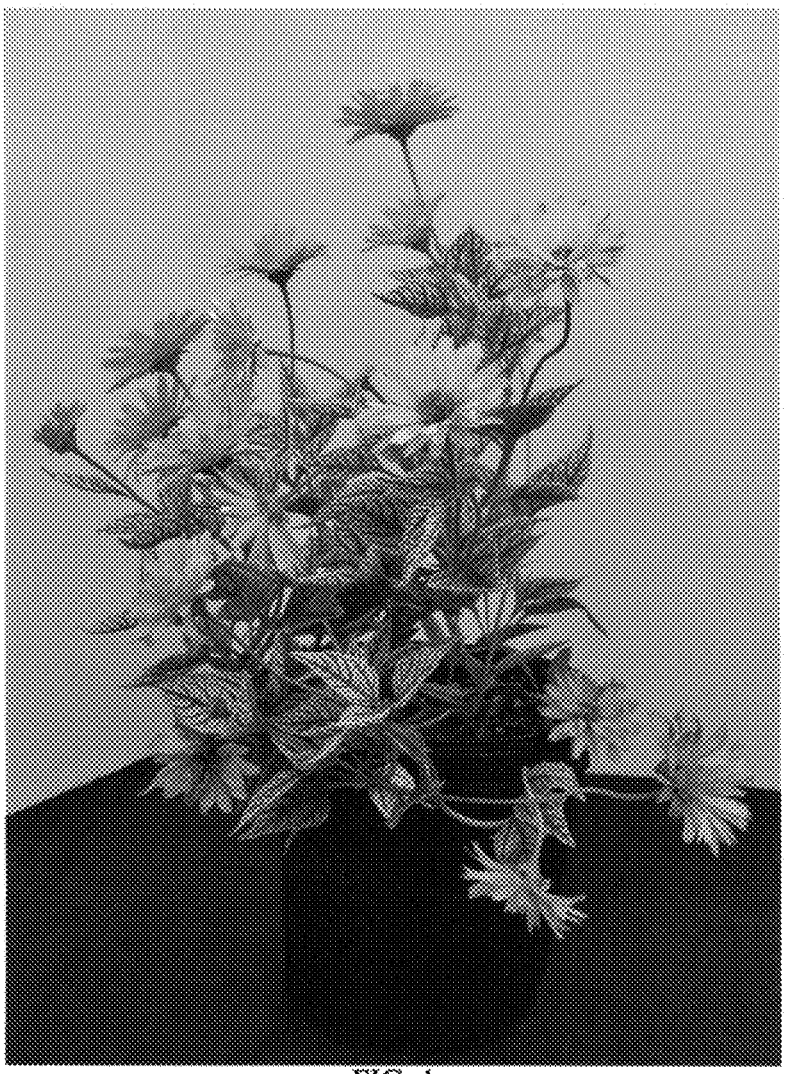
FIG. 1 illustrates a side view of the overall growth and flowering habit of 'Double Sunstruck'.
Figure 2:
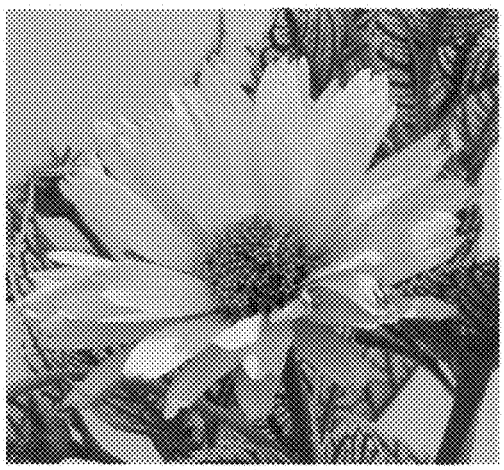
FIG. 2 illustrates a close-up view of an individual inflorescence of 'Double Sunstruck'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2014 under natural light conditions in West Chicago, Ill.

The following descriptions and measurements describe plants produced from cuttings from stock plants and grown under conditions comparable to those used in commercial practice. The plants were grown in 1.5 gallon containers for approximately two months in a greenhouse and 11 weeks outdoors in West Chicago, Ill. Plants were given two pinches prior to transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Heliopsis helianthoides* cultivar Double Sunstruck.

Parentage:

*Female parent.*—Proprietary *Heliopsis helianthoides* breeding selection coded 3652-C3, not patented.

*Male parent.*—Proprietary *Heliopsis helianthoides* breeding selection coded 3645-A2, not patented.

Propagation:

*Type cutting.*—Terminal stem.

*Time to initiate roots.*—Approximately 10 to 12 days.

*Time to produce a rooted cutting.*—Approximately 35 to 42 days.

*Root description.*—Fibrous.

*Rooting habit.*—Freely branching.

Plant description:

*Commercial crop time.*—Approximately 10 to 12 weeks from a rooted cutting to finish in a 10 cm pot.

*Growth habit and general appearance.*—Moderately vigorous, compact-mounded.

*Size.*—Height from soil level to top of plant plane: Approximately 32.5 cm. Width: Approximately 49.0 cm.

*Branching habit.*—Freely branching, pinching enhances basal branching. Quantity of main branches per plant: Approximately 7.

*Branch.*—Strength: Strong, somewhat flexible. Length to base of inflorescence: Approximately 16.0 cm. Diameter: Approximately 3.0 mm. Length of central internode: Approximately 2.7 cm. Texture: Sparsely pubescent. Color of young stem: 146C. Color of mature stem: 146C tinted 187A in sun.

Foliage description:

*General description.*—Quantity of leaves per main branch: Approximately 10. Fragrance: None. Form: Simple. Arrangement: Opposite.

*Leaves.*—Aspect: Petiole is at an acute angle to stem blade is primarily perpendicular to stem. Shape: Ovate. Margin: Serrate. Apex: Acute. Base: Attenuate. Venation pattern: Pinnate. Length of mature leaf: Approximately 6.5 cm. Width of mature leaf: 3.7 cm. Texture of upper surface: Moderately pubescent. Texture of lower surface: Moderately pubescent, densely pubescent on venation. Color of upper surface of young foliage: 155A with venation of N137A. Color of lower surface of young foliage: 155A with venation of N137C. Color of upper surface of mature foliage: 155A with an overlay and venation of N137A, overlay becomes heavier with age. Color of lower surface of mature foliage: 155A with an overlay and venation of N137C, overlay becomes heavier with age.

*Petiole.*—Length: Approximately 1.5 cm. Diameter: Approximately 2.0 mm. Texture: Moderately pubescent. Color: 146D.

Flowering description:

*Flowering habit.*—'Double Sunstruck' is freely flowering under outdoor growing conditions with substantially continuous blooming from early spring through summer.

*Lastingness of individual inflorescence on the plant.*—Approximately 4 weeks.

Inflorescence description:

*General description.*—Type: Semi-double composite, actinomorphic. Persistent. Shape: Round. Aspect: Upward and outward facing. Arrangement: Terminal capitulum, positioned above the foliage. Quantity per plant: Approximately 14. Diameter: Approximately 7.0 cm. Depth: Approximately 3.0 cm. Fragrance: Slight.

*Peduncle.*—Strength: Strong, somewhat flexible. Aspect: Erect. Length: Approximately 10.0 cm. Diameter: Approximately 2.0 mm. Texture: Densely pubescent. Color: 146C.

*Bud.*—Rate of opening: Generally takes 5 to 7 days for bud to progress from first color to fully open flower. Quantity per plant: Approximately 4.

*Bud just before opening.*—Shape: Flattened globular. Diameter: Approximately 1.2 cm. Color: 144D.

*Ray florets.*—Quantity per inflorescence: Approximately 28 to 32. Appearance: Dull. Arrangement: Imbricate in two to three whorls. Aspect: Acute angle to disc, outer whorl becoming perpendicular with age. Shape: Oblanceolate. Margin: Entire. Apex: Three acute tips. Base: Attenuate. Length: Approximately 3.0 cm. Width: Approximately 9.0 mm. Texture of upper and lower surfaces: Glabrous, ribbed longitudinally. Color of upper surface when first open: 23A. Color of lower surface when first open: 15B. Color of upper surface when fully open: 21B, transitioning to 14A with age. Color of lower surface when fully open: 15B, transitioning to 14C with age.

*Disc florets.*—Quantity per inflorescence: Approximately 125. Arrangement: Massed in center of inflorescence Shape: Tubular. Margin: Entire. Apex: Five acute tips. Base: Fused. Length: Approximately 1.0 cm. Diameter at apex: Approximately 2.5 mm. Diameter at base: Approximately 1.0 mm. Texture: Glabrous. Color when fully open: 23A at tips, centers of 1B and NN155A at base.

*Disc.*—Diameter: Approximately 1.8 cm. Depth: Approximately 1.5 cm.

*Receptacle.*—Shape: Conical. Height: Approximately 5.0 mm. Diameter at base: Approximately 1.0 cm. Color: 155C.

*Phyllaries.*—Quantity per inflorescence Approximately 24. Arrangement: In two whorls. Shape: Linear. Margin: Entire. Apex: Broadly acute. Base: Truncate. Length: Approximately 1.0 cm. Width: Approximately 4.0 mm. Texture of upper and lower surfaces: Densely pubescent. Color of upper and lower surfaces: 137A with base of 138B.

*Reproductive organs.*—Androecium: Present on disc florets only. Stamen quantity: 5.0. Stamen length: Approximately 6.0 mm. Anther shape: Linear. Anther length: Approximately 3.0 mm. Anther color: Closest to 203B. Filament color: 155D. Pollen amount: Abundant. Pollen color: 23A. Gynoecium: Present on ray and disc florets. Pistil quantity: 1 per floret. Pistil length: Approximately 1.0 cm. Stigma shape: Bifid. Stigma length: Approximately 2.0 mm. Stigma color: 23A. Style length: Approximately 5.0 mm. Style color: Between 150C and 150D. Ovary length: Approximately 3.0 mm. Ovary color: NN155A.

Seed and fruit production: Neither seed nor fruit production has been observed.

Disease and pest resistance: Resistance to pathogens and pests common to *Heliopsis* has not been observed.

What is claimed is:

1. A new and distinct cultivar of *Heliopsis* plant named 'Double Sunstruck', substantially as herein shown and described.

* * * * *